United States Patent [19]

Bey et al.

[11] 4,134,918

[45] Jan. 16, 1979

[54] ALPHA-HALOMETHYL DERIVATIVES OF AMINES

[75] Inventors: Philippe Bey, Strasbourg; Michel Jung, Illkirch Graffenstaden, both of France

[73] Assignee: Merrell Toraude et Compagnie, Strasbourg, France

[21] Appl. No.: 830,998

[22] Filed: Sep. 6, 1977

[51] Int. Cl.² .............. C07C 87/22; C07C 69/02; C07C 103/10; C01B 25/26
[52] U.S. Cl. .......... 260/583 GG; 260/558 A; 260/558 S; 260/559 T; 260/559 A; 260/561 R; 260/561 A; 260/561 S; 260/564 A; 260/570.5 S; 260/583 EE; 260/583 G; 536/26; 560/29; 560/30; 560/148; 560/158; 560/159; 560/161; 424/244; 424/300; 424/316; 424/320; 424/325; 424/330
[58] Field of Search .... 260/583 EE, 583 G, 583 GG, 260/, 583 P, 564 A, 570.5 S, 561 R, 561 A, , 558 A, 559 A; 536/26; 560/30, 159, 161; 424/300, 320, 325

[56] References Cited

U.S. PATENT DOCUMENTS 2,515,246  7/1950  McBee et al. .......... 260/583 G
2,769,839  11/1956  Fincke .............. 260/583 EE X

FOREIGN PATENT DOCUMENTS 677908  1/1964  Canada ............... 260/583 EE
2018461  11/1971  Fed. Rep. of Germany .... 260/583 EE

OTHER PUBLICATIONS

Sidgwick, "The Organic Chemistry of Nitrogen", Third Edition, p. 100 (1966).
Patai, "The Chemistry of the Amino Group", pp. 670-672 (1968).
Westland et al, "Index Chemicus", 30, 100145 (1968).
Maynard, "Chem. Ab.", vol. 57, Ab. No. 4520 d (1962).

Primary Examiner—Winston A. Douglas
Assistant Examiner—John Doll
Attorney, Agent, or Firm—L. Ruth Hattan; Eugene O. Retter; George W. Rauchfuss, Jr.

[57] ABSTRACT

Novel halomethyl derivatives of amines of the following general structure:

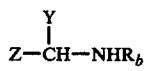

wherein Y is $FCH_2-$, $F_2CH-$ or $F_3C-$; Z is β-methylthioethyl, β-benzylthioethyl, S-(5'-desoxyadenosin-5'-yl)-S-methylthioethyl, γ-guanidinopropyl, or

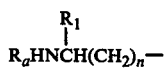

wherein n is 2 or 3 and $R_1$ is hydrogen or lower alkyl of from 1 to 4 carbon atoms with the proviso that when $R_1$ is other than hydrogen, n is 2; and each of $R_a$ and $R_b$ is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched, or

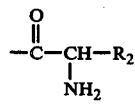

wherein $R_2$ is hydrogen, a straight or branched lower alkyl group of from 1 to 4 carbon atoms, benzyl or p-hydroxybenzyl; with the provisos that when Z is β-benzylthioethyl or S-(5'-desoxyadenosin-5'-yl)-S-methylthioethyl, $R_b$ is hydrogen, when Z is β-methylthioethyl, Y is other than $F_3C-$, and when Z is

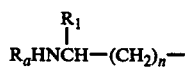

each of $R_a$ and $R_b$ can be the same or different; and pharmaceutically acceptable salts and individual optical isomers thereof.

10 Claims, No Drawings

ALPHA-HALOMETHYL DERIVATIVES OF AMINES

FIELD OF INVENTION

This invention relates to novel pharmaceutically useful halomethyl derivatives of amines.

SUMMARY OF INVENTION

The compounds of the present invention may be represented by the following general Formula I:

$$Z-\overset{\overset{Y}{|}}{C}HNHR_b \qquad \text{Formula I}$$

In the above general Formula I Y is $FCH_2-$, $F_2CH-$, or $F_3C-$; Z is β-methylthioethyl, β-benzylthioethyl, S-(5'-desoxyadenosin-5'-yl)-S-methylthioethyl, γ-guanidinopropyl, or

each of $R_a$ and $R_b$ can be the same or different. Pharmaceutically acceptable salts and individual optical isomers of the compounds of general Formula I are also included within the scope of the present invention.

DETAILED DESCRIPTION OF INVENTION

In the above general Formula I in addition to the group

the symbol Z represents the substituent groups β-methylthioethyl, β-benzylthioethyl, S-(5'-desoxyadenosin-5'-yl)-S-methylthioethyl and β-guanidinopropyl which are depicted by the following structures:

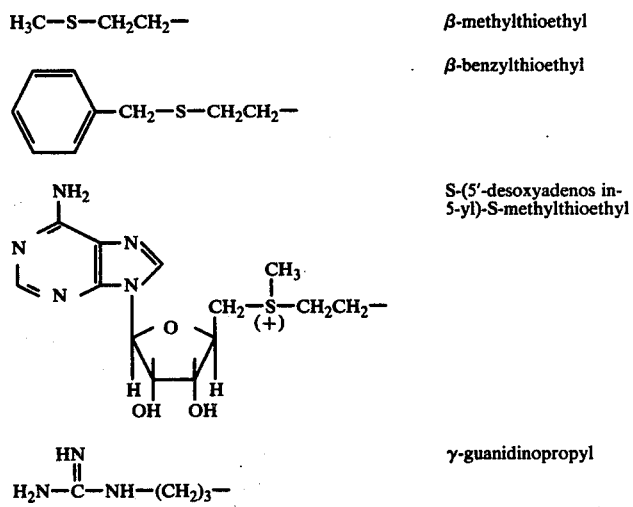

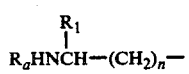

wherein n is the integer 2 or 3 and $R_1$ is hydrogen or a lower alkyl group of from 1 to 4 carbon atoms with the proviso that when $R_1$ is other than hydrogen, n is 2; and each of $R_a$ and $R_b$ is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched, or the group

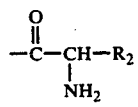

wherein $R_2$ is hydrogen, a straight or branched lower alkyl group of from 1 to 4 carbon atoms, benzyl or p-hydroxybenzyl; with the provisos that when Z is β-benzylthioethyl or S-(5'-desoxyadenosin-5'-yl)-S-methylthioethyl, $R_b$ is hydrogen, when Z is β-methylthioethyl, Y is other than $F_3C-$, and when Z is As used in general Formula I the term alkylcarbonyl is taken to mean the group

wherein the alkyl moiety has from 1 to 4 carbon atoms and is straight or branched, for example, methyl, ethyl, n-propyl, isopropyl, n-butyl, isobutyl and tert-butyl.

As used in general Formula I the term alkoxycarbonyl is taken to mean the group

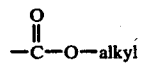

wherein the alkoxy moiety, that is, -O-alkyl, has from 1 to 4 carbon atoms and is straight or branched, for example, methoxy, ethoxy, n-propoxy, isopropoxy, n-butoxy, and tert-butoxy.

Illustrative examples of straight or branched alkyl groups having from 1 to 4 carbon atoms as used in general Formula I are methyl, ethyl, n-propyl, n-butyl, isopropyl and tert-butyl.

Illustrative examples of pharmaceutically acceptable salts of the compounds of this invention include nontoxic acid addition salts formed with inorganic acids, such as, hydrochloric, hydrobromic, sulfuric and phosphoric acid, and organic acids, such as, methane sulfonic, salicylic, maleic, malonic, tartaric, citric, cyclamic and ascorbic acids.

Preferred compounds of this invention are those of general Formula I wherein Z is β-methylthioethyl, S-(5'-desoxyadenosin-5'-yl)-S-methylthioethyl, γ-guanidinopropyl or

and each of $R_a$ and $R_b$ is hydrogen. More preferred compounds of this invention are those of general Formula I wherein Z is

with compounds wherein $R_1$ is hydrogen and n is 2 being most preferred.

Illustrative examples of compounds of the present invention are the following:
1-difluoromethyl-3-methylthiopropylamine,
1-trifluoromethyl-3-benzylthiopropylamine,
1-fluoromethyl-3-[S-(5'-desoxyadenosin-5'-yl)-S-(methyl)-thio]propylamine,
1-fluoromethyl-4-guanidinobutylamine,
1-difluoromethyl-1,4-butanediamine,
1-difluoromethyl-1,5-pentanediamine,
N-(1-fluoromethyl-4-aminobutyl)acetamide,
1-difluoromethyl-4-guanidinobutylamine,
1-trifluoromethyl-4-guanidinobutylamine,
1-fluoromethyl-1,4-butanediamine,
1-trifluoromethyl-1,4-butanediamine,
1-fluoromethyl-1,5-pentanediamine,
1-trifluoromethyl-1,5-pentanediamine,
N-(1-difluoromethyl-4-aminobutyl)propionamide,
N-(1-difluoromethyl-3-methylthiopropyl)butyramide,
methyl N-(1-trifluoromethyl-4-aminobutyl)carbamate,
ethyl N-(1-difluoromethyl-5-aminopentyl)carbamate,
1-difluoromethyl-1,4-butylene-bis-tert-butyramide,
N-(1-fluoromethyl-4-aminobutyl)-2-aminoacetamide,
N-(1-difluoromethyl-5-aminopentyl)-2-aminodihydrocinnamide,
N-(1-fluoromethyl-3-methylthiopropyl)-2-amino-p-hydroxydihydrocinnamide,
N-(1-difluoromethyl-4-guanidinobutyl)-2-aminoacetamide,
1-difluoromethyl-1,4-pentanediamine, and
1-difluoromethyl-1,4-hexanediamine.

The compounds of general Formula I have many utilities. The compound of general Formula I wherein Z is β-benzylthioethyl, and $R_b$ is hydrogen is useful as an intermediate in the preparation of the corresponding pharmaceutically useful compound wherein Z is S-(5'-desoxyadenosin-5'-yl)-S-methylthioethyl.

The compounds of general Formula I wherein Z is other than γ-benzylthioethyl are irreversible inhibitors of decarboxylase enzymes which are involved in polyamine formation rendering said compounds useful as pharmacological agents. Polyamines, particularly putrescine, spermidine and spermine are present in plant and animal tissues and in some microorganisms. Although the exact physiological role of polyamines has not been clearly delineated there is evidence to suggest that polyamines are involved with cell division and growth. (H. G. Williams-Ashman et al., The Italian J. Biochem. 25, 5–32 (1976), A. Raina and J. Jänne, Med. Biol. 53, 121–147 (1975) and D. H. Russell, Life Sciences 13, 1635–1647 (1973)). Polyamines are essential growth factors for or involved in the growth processes of certain microorganisms, for example, E. coli, Enterobacter, Klebsiella, Staphylococcus aureus, C. cadaveris, Salmonella typhosa and Haemophilus parainfluenza. Polyamines are associated with both normal and neoplastic rapid growth there being an increase in the synthesis and accumulation of polyamines following a stimulus causing cellular proliferation. Also, levels of polyamines are known to be high in embryonic systems, the testes, in patients with rapidly growing tumors, leukemic cells and other rapidly growing tissues. It is known that there is a correlation between the activity of the decarboxylase enzymes of ornithine, S-adenosylmethionine, arginine and lysine and polyamine formation.

The biosyntheses of putrescine, spermidine and spermine are interrelated. Putrescine is the decarboxylation product of ornithine, catalyzed by ornithine decarboxylase. Putrescine formation may also occur by decarboxylation of arginine to form agmatine which is hydrolyzed to give putrescine and urea. Arginine is also involved in ornithine formation by action of the enzyme arginase. Activation of methionine by S-adenosylmethionine synthetase forms S-adenosylmethionine which is decarboxylated, after which the propylamine moiety of activated methionine may be transferred to putrescine to form spermidine or the polyamine moiety may be transferred to spermidine to form spermine. Hence, putrescine serves as a precursor to spermidine and spermine and additionally has been shown to have a marked regulatory effect upon the polyamine biosynthetic pathway in that it has been shown that increased synthesis of putrescine is the first indication that a tissue will undergo renewed growth processes. Cadaverine which is the decarboxylation product of lysine has been shown to stimulate the activity of S-adenoxylmethionine decarboxylase and is known to be essential to growth processes of many microorganisms, for example, H. parainfluenza.

The compounds of general Formula I wherein Z is

are irreversible inhibitors of ornithine decarboxylase and lysine decarboxylase respectively as n varies from 2 to 3. The compounds of general Formula I wherein Z is β-methylthioethyl or S-(5'-desoxyadenosin-5'-yl)-S-methylthioethyl are irreversible inhibitors of S-adenosylmethionine decarboxylase and wherein Z is γ-guanidinopropyl are irreversible inhibitors of arginine decarboxylase. As irreversible inhibitors of the above-enumerated decarboxylase enzymes the compounds of general Formula I wherein Z is other than β-benzylthioethyl are useful as antiinfective agents being effective in the control of microorganisms, for example, bacteria, fungi and viruses which are dependent upon polyamines for growth, for example, E. coli, Enterobacter, Klebsiella, Staphylococcus aureus, C. cadaveris, viruses such as, H. parainfluenza, picornaviruses, for example, encephalomyocarditis, *herpes simplex*, poxviruses and arboviruses, for example, *Semliki forest*. The compounds of general Formula I wherein Z is other than β-benzylthioethyl and

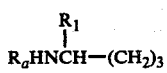

are also useful in the control of certain rapid growth processes, and can be used alone or in combination with one another. For example, the compounds are useful in the inhibition of spermatogenesis and embryogenesis and therefore the compounds find use as male antifertility agents and abortifacients. The compounds are also useful in the inhibition of the immune response, thus the compounds are useful as immunosuppressants for the treatment, for example, of myasthenia gravis, arthritis, multiple sclerosis and the prevention of tissue or organ transplant rejection, and are useful in the control of neoplastic growth, for example, solid tumors, leukemias and lymphomas. The compounds are also useful as inhibitors of abnormal cutaneous cell growth as found with a psoriatic condition.

The utility of compounds of general Formula I as irreversible inhibitors of ornithine or S-adenosylmethionine decarboxylases in vivo can be demonstrated as follows. An aqueous solution of an appropriate compound of Formula I is given orally or parenterally to male mice or rats. The animals are sacrificed 1 to 48 hours after administration of the compound and the ventral lobes of the prostate removed and homogenized with the activity of ornithine and S-adenosylmethionine decarboxylases being measured as generally described by E. A. Pegg and H. G. Williams-Ashman, Biochem. J. 108, 533–539 (1968) and J. Janne and H. G. Williams-Ashman, Biochem. and Biophys. Res. Comm. 42, 222–228 (1971).

In administering the compounds of general Formula I wherein Z is

wherein n is 2 or 3 and $R_1$ is hydrogen it may be desirable to administer concurrently by known procedures a monoamine oxidase inhibitor such as trans(±)-2-phenylcycloproponamine or N-benzyl-N-methyl-2-propynylamine.

The compounds of general Formula I wherein Z is

wherein n is the integer 2 or 3 and $R_1$ is hydrogen are metabolic precursors of compounds of the following structure

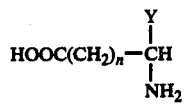

wherein n is the integer 2 or 3 and Y has the meaning defined in Formula I which are known to be irreversible inhibitors of γ-aminobutyric acid transaminase and upon administration results in higher brain levels of γ-aminobutyric acid (GABA). As precursors of γ-mono, di or tri-fluoromethyl β-aminobutyric acid the above-described compounds of Formula I are useful in the treatment of disorders of the central nervous system consisting of involuntary movement associated with Huntington's chorea, Parkinsonism, extrapyramidal effects of drugs, for example, neuroleptic seizure disorders associated with epilepsy, alcohol withdrawal, psychoses associated with schizophrenia, depression, manic depression and hyperkinesis.

Several previous studies have shown that γ-aminobutyric acid is a major inhibitory transmitter of the central nervous system as reported, for example, by Y. Godin et al., Journal Neurochemistry, 16, 869 (1969) and that disturbance of the excitation and inhibition interplay can lead to diseased states such as Huntington's chorea (The Lancet, November 9, 1974, pp. 1122–1123) Parkinsonism, schizophrenia, epilepsy, depression, hyperkinesis and manic depression disorders, Biochem. Pharmacol. 23 2637–2649 (1974).

That the compounds of general Formula I wherein Z is

wherein n is 2 or 3 and $R_1$ is hydrogen are converted metabolically to the compounds of Formula II may be demonstrated by the protective effective of the compounds on audiogenic seizures in mice of the DBA strain measured by the general method described by Simler et al., Biochem. Pharmacol. 22, 1701 (1973) which is currently used to evidence antiepileptic activity.

The compounds of general Formula I wherein $R_b$ is hydrogen are useful as chemical intermediates for the preparation of novel cephalosporin in derivatives which are useful as antibiotics and have the following general structure:

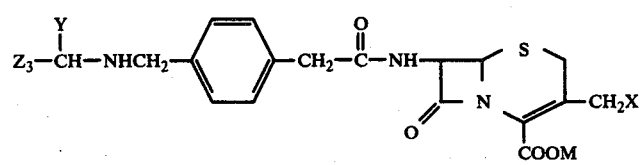

wherein Y has the meaning defined in Formula I, $Z_3$ is β-methylthioethyl, β-benzylthioethyl, S-(5′-desoxyadenosin-5′-yl)-S-methylthioethyl, γ-guanidinopropyl or

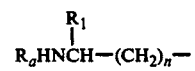

wherein n is 2 or 3, $R_1$ is hydrogen or lower alkyl of from 1 to 4 carbon atoms and $R_a$ is hydrogen; M is hydrogen or a negative charge; and X is hydrogen or acetoxy with the proviso that when $Z_3$ is β-methylthioethyl, Y is other than $F_3C$— and when $R_1$ is other than hydrogen, n is the integer 2.

The compounds of general Formula III and the pharmaceutically acceptable salts and individual optical isomers thereof are novel compounds useful as antibiotics and can be administered in a manner similar to that of many well known cephalosporin derivatives, for example, cephalexin, cephalothin, or cephaloglycine. The compounds of general Formula III and pharmaceutically acceptable salts and isomers thereof can be administered alone or in the form of pharmaceutical preparations either orally or parenterally and topically to warm blooded animals, that is, birds and mammals, for example, cats, dogs, bovine cows, sheep, horses and humans. For oral administration the compounds can be administered in the form of tablets, capsules or pills or in the form of elixirs or suspensions. For parenteral administration, the compounds may best be used in the form of a sterile aqueous solution which may contain other solutes, for example, enough saline or glucose to make the solution isotonic. For topical administration the compounds of general Formula III, salts and isomers thereof may be incorporated into creams or ointments.

Illustrative examples of bacteria against which the compounds of general Formula III and the pharmaceutically acceptable salts and individual optical isomers thereof are active are *Staphylococcus aureus, Salmonella schotmuehleri, Klebsiella pneumoniae, Diplococcus pneumoniae* and *Streptococcus pyogenes*.

Illustrative pharmaceutically acceptable non-toxic inorganic acid addition salts of the compounds of general Formula III are mineral acid addition salts, for example, hydrogen chloride, hydrogen bromide, sulfates, sulfamates, phosphate, and organic acid addition salts are, for example, maleate, acetate, citrate, oxalate, succinate, benzoate, tartrate, fumarate, malate and ascorbate. The salts can be formed by conventional means.

Illustrative examples of compounds of general Formula III are 7-[[2-[4-(1-difluoromethyl-4-aminobutylaminomethyl)phenyl]acetyl]amino]-3-acetyloxymethyl-8-oxo-5-thia-1-azabicyclo[4.2.0]oct-2-ene-2-carboxylic acid, 7-[[2-[4-(1-fluoromethyl-3-methylthiopropylaminomethyl)phenyl]acetyl]amino]-3-acetyloxymethyl-8-oxo-5-thia-1-azabicyclo[4.2.0]oct-2-ene-2-carboxylic acid and 7-[[2-[4-(1-fluoromethyl-5-aminopentylaminomethyl)phenyl]acetyl]-amino]-3-acetyloxymethyl-8-oxo-5-thia-1-azabicyclo[4.2.0]oct-2-ene-2-carboxylic acid.

The preparation of the compounds of general Formula III is described hereinbelow.

As pharmacologically useful agents the compounds of general Formula I wherein Z is other than β-benzylthioethyl can be administered in various manners to the patient being treated to achieve the desired effect. The compounds can be administered alone or in the form of a pharmaceutical preparation orally, parenterally, for example, intravenously, intraperitoneally, or subcutaneously, or topically. The amount of compound administered will vary over a wide range and can be any effective amount. Depending on the patient to be treated, the condition being treated and the mode of administration, the effective amount of compound administered will vary from about 0.1 mg/kg to 500 mg/kg of body weight of the patient per unit dose and preferably will be about 10 mg/kg to about 100 mg/kg of body weight of patient per unit dose. For example, a typical unit dosage form may be a tablet containing from 10 to 300 mg of a compound of Formula I which may be administered to the patient being treated 1 to 4 times daily to achieve the desired effect.

As used herein the term patient is taken to mean warm blooded animals such as mammals, for example, cats, dogs, rats, mice, guinea pigs, horses, bovine cows, sheep and humans.

The solid unit dosage forms can be of the conventional type. Thus, the solid form can be a capsule which can be of the ordinary gelatin type containing a novel compound of this invention and a carrier, for example, lubricant and inert fillers such as lactose, sucrose and corn starch. In another embodiment, the novel compounds are tableted with conventional tablet bases such as lactose, sucrose or corn starch in combination with binders such as acacia, corn starch or gelatin, disintegrating agents such as corn starch, potato starch, or alginic acid, and a lubricant such as stearic acid, or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general, water, saline, aqueous dextrose, and related sugar solutions, ethanols and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

(PROCESS A)

The compounds of general Formula I wherein Z is β-methylthioethyl, β-benzylthioethyl, or

and wherein each of $R_a$ and $R_b$ is hydrogen are prepared by reducing a ketone of the formula

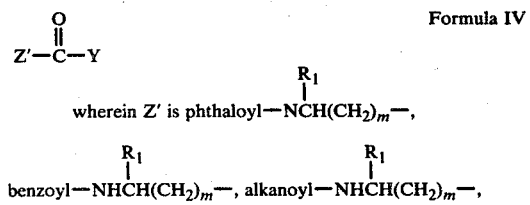

Formula IV

-continued

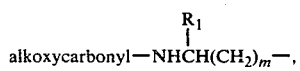

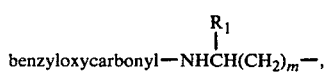

β-methylthioethyl or β-benzylthioethyl wherein m is the integer 2 or 3, the alkanoyl moiety has from 2 to 5 carbon atoms and is straight or branched, the alkoxy moiety has from 1 to 4 carbon atoms and is straight or branched and Y and $R_1$ have the meanings defined in general Formula I with the proviso that when Y is $F_3C—$, Z' is other than β-methylthioethyl,

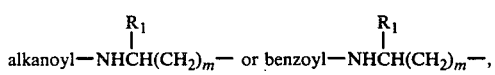

to the corresponding alcohol which is treated with one equivalent of an imide, such as, phthalimide, succinimide or maleimide, 1.1 equivalents of a phosphine, for example, triphenylphosphine or a trialkylphosphine, such as, tri-n-butylphosphine and 1.1 equivalents of diethyl azodicarboxylate in a suitable solvent, such as ethers, for example, diethyl ether, tetrahydrofuran or p-dioxane, benzene or dimethoxyethane at about 0° to 100° C, preferably about 25° C for about one-half hour to 24 hours under an inert atmosphere, for example, nitrogen or argon and hydrolyzing the thus obtained imido derivative to the free amine.

Reduction of the ketones of Formula IV to the corresponding alcohol is achieved chemically using, for example, 1 to 10 equivalents of a metal hydride reducing reagent, such as lithium borohydride, sodium borohydride, sodium cyanoborohydride, or lithium aluminum hydride, borane or dimethylthioborane or catalytically using, for example, Raney nickel, rhodium, palladium on charcoal, or platinum oxide. Overall the reaction time varies from about 10 minutes to 24 hours and the temperature varies from about −40° C to 100° C depending on the reducing reagent employed,. When chemial reducton is employed the reaction time generally varies from about 10 minutes to 24 hours with temperatures varying from about −40° C to 65° C. Suitable solvents for chemical reduction of compounds of general Formula IV include lower alcohols, such as, methanol or ethanol or ethers, such as, diethyl ether or tetrahydrofuran. When catalytic reduction is employed the reaction time varies from about 1 hour to 24 hours, the reaction temperature varies from about 25° to 100° C and the pressure varies from 1 to 120 atmospheres. Suitable solvents for catalytic reduction of compounds of general Formula IV include lower alcohols, for example, methanol or ethanol, acetic acid, or ethyl acetate. Chemical reduction is preferred.

Hydrolysis to the amine and to remove any distal amine protecting group is achieved using a strong mineral acid, for example, hydrochloric acid, hydrobromic acid or sulfuric acid or an organic acid, for example, toluene sulfonic acid or trifluoroacetic acid in water at reflux temperature for about 4 to 48 hours, or using, for example, 1 to 3 equivalents of hydrazine, methylhydrazine or methylamine at a temperature of from about 25° C to reflux for about 1 to 12 hours followed by treatment with a strong mineral acid or organic acid as described above.

As indicated above tri-alkylphosphines, such as, tri-n-butylphosphine may be employed in the reaction. The term alkyl is taken to mean an alkyl group having from 1 to 10 carbon atoms. The tri-alkylphosphines are known in the art or may be obtained by procedures generally known in the art.

As used in general Formula IV the term

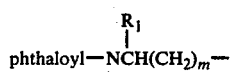

is taken to mean the group

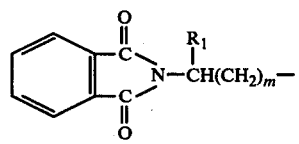

wherein m is the integer 2 or 3 and $R_1$ has the meaning defined in Formula I, the term

is taken to mean the group

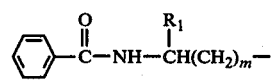

wherein m is the integer 2 or 3 and $R_1$ has the meaning defined in Formula I; the term

is taken to mean the group

wherein the alkyl moiety has from 1 to 4 carbon atoms and is straight or branched, m is the integer 2 or 3, and $R_1$ has the meaning defined in general Formula I; the term

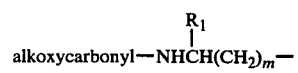

is taken to mean the group

wherein the alkoxy moiety has from 1 to 4 carbon atoms and is straight or branched, m is the integer 2 or 3 and $R_1$ has the meaning defined in general Formula I; the term

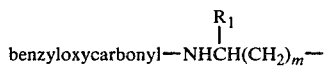

is taken to mean the group

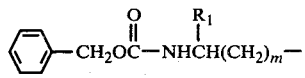

wherein m is the integer 2 or 3 and $R_1$ has the meaning defined in Formula I. The terms β-methylthioethyl and β-benzylthioethyl as used in general Formula IV are the same as defined in general Formula I.

(PROCESS B)

The compounds of general Formula I wherein Z is β-methylthioethyl, β-benzylthioethyl or

wherein each of $R_a$ and $R_b$ is hydrogen and n is the integer 2 or 3 may also be prepared by treating a ketone of Formula IV with ammonia or an ammonium slat of a mineral or organic acid, illustratively, ammonium chloride, ammonium acetate, ammonium bromide or ammonium nitrate and a reducing agent such as sodium cyanoborohydride or lithium cyanoborohydride in a suitable solvent, for example, lower alcohols such as methanol or ethanol, acetonitrile, dimethoxyethane, ethers such as p-dioxane, diethylether, tetrahydrofuran or dimethylformamide for about 1 hour to 3 days at a temperature of about 0° to 100° C, preferably at about 25° C and a pH of about 6 to 8, followed by hydrolysis to remove any distal amine protecting group.

Hydrolysis to remove any distal amine protecting group is achieved using a strong mineral acid, for example, hydrochloric acid, hydrobromic acid or sulfuric acid or an organic acid, for example, toluenesulfonic acid or trifluoroacetic acid in water at reflux temperature for about 4 to 48 hours, or using, for example, 1 to 3 equivalents of hydrazine, methylhydrazine or methylamine at a temperature of from about 25° C to reflux for about 1 to 12 hours followed by treatment with a strong mineral acid or organic acid as described above.

The compounds of general Formula I wherein Z is γ-guanidinopropyl are prepared from the corresponding derivative wherein Z is

wherein $R_1$ is hydrogen, that is, the compound

  2 $HX_1$  Formula V wherein Y has the meaning defined in Formula I, $X_1$ is halogen, for example, chlorine and $R_b$ has the meaning defined in Formula I with the proviso that any free amino group is suitably protected with, for example, benzyloxycarbonyl, by treatment with an alkylisothiouronium salt, for example, ethylisothiouronium hydrobromide by procedures generally known in the art; for example, Organic Synthesis, III, p. 440 (1955). The reaction is carried out in the presence of a base, such as aqueous sodium hydroxide or potassium hydroxide at a pH of about 10 at a temperature of about 25° C for about 6 to 60 hours after which the reaction mixture is neutralized with concentrated hydrochloric acid and the product isolated. When appropriate, protecting groups are removed by acid hydrolysis, for example, by treatment with HBr in dioxane. The preparation of compounds of Formula V is described hereinbelow.

The compounds of Formula I wherein Z is S-(5'-desoxyadenosin-5'-yl)-S-methylthioethyl and $R_b$ is hydrogen are prepared by treating for about one hour the corresponding compound wherein Z is β-benzylthioethyl, that is, the compound

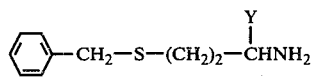  Formula VI

Formula VI with sodium amide or lithium amide in liquid ammonia followed by the addition of finely divided sodium or lithium metal until the blue color persists, and reacting the thus obtained di-metal salt with the -p-toluenesulfonyladenosine, 5-bromoadenosine or 5-chloroadenosine having the structure, optionally protected as the 2′, 3′-isopropylidene

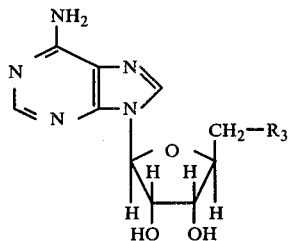  Formula VII wherein $R_3$ is p-toluenesulfonyl, chlorine or bromine for about two hours in liquid ammonia followed by acid hydrolyis and treatment with methyl iodide in acidic solvents such as formic acid, acetic acid, trifluoroacetic acid or trichloroacetic acid or mixtures thereof. The compounds of Formula VII may be obtained from adenosine by procedures well known in the art.

It is evident from the foregoing that certain compounds of general Formula I wherein $R_a$ is other than hydrogen are formed in situ. In PROCESS A hydrolysis may be achieved by treatment with acid or by treatment with hydrazine, phenylhydrazine or methylamine followed by treatment with acid. Treatment with hydrazine, phenylhydrazine or methylamine alone, that is deletion of the subsequent acid hydrolysis when Z′ represents

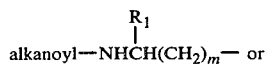 or

or
results in compounds of Formula I wherein Z is $R_a HNCH(CH_2)_m—$
 $|$
 $R_1$ wherein $R_a$ is alkylcarbonyl wherein the alkyl moiety is straight or branched and has from 1 to 4 carbon atoms or alkoxycarbonyl wherein the alkoxy moiety has from 1 to 4 carbon atoms and is straight or branched respectively. Similarly, when in PROCESS B Z' represents the group

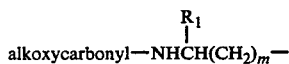
alkoxycarbonyl—NHCH(CH$_2$)$_m$— and the hydrolysis step is deleted compounds of Formula I wherein $R_a$ is alkoxycarbonyl wherein the alkoxy moiety has from 1 to 4 carbon atoms and is straight or branched are obtained.

Following is described the preparation of compounds of general Formula I, other than compounds wherein Z is γ-guanidinopropyl, wherein $R_a$ and/or $R_b$ are other than hydrogen, that is, compounds of general Formula I wherein Z is β-methylthioethyl and $R_b$ is other than hydrogen and compounds wherein Z is

$R_aHNCH(CH_2)_n$— wherein either or both of $R_a$ and $R_b$ is other than hydrogen including compounds of Formula V. The following description is applicable to all the above said compounds, however, in preparing compounds wherein Z is

$R_aHNCH(CH_2)_n$— it is necessary to protect one or the other of the amino groups prior to treatment with the appropriate reactant, that is, acid halide or anhydride, alkyl haloformate or acid of the formula

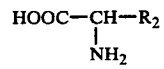
HOOC—CH—R$_2$
          |
          NH$_2$ or anhydride thereof as described below to give compounds wherein either of $R_a$ and $R_b$ is other than hydrogen or both $R_a$ and $R_b$ are other than hydrogen and are different as follows: When $R_a$ is hydrogen and $R_b$ is other than hydrogen, the amino group to which $R_a$ is attached is protected as a phthalimido derivative by treating the corresponding derivative wherein $R_a$ is hydrogen with a carbalkoxyphthalimide wherein the alkoxy moiety has from 1 to 4 carbon atoms, for example, carbethoxyphthalimide in a solvent such as an ether or a lower alcohol, such as, methanol, for ½ to 3 hours at about 0° to 50° C followed by extraction with acid, for example, hydrochloric acid prior to treatment with the appropriate reactant described below to give compounds wherein $R_b$ is other than hydrogen. The phthalimide group is subsequently removed by treatment with hydrazine in a lower alcohol solvent, such as, methanol at about 50° to 100° C for about 1 to 4 hours. The thus obtained compounds, that is, compounds wherein $R_a$ is hydrogen and $R_b$ is other than hydrogen may be treated with the appropriate reactants described below to give compounds wherein $R_a$ and $R_b$ are both other than hydrogen and may be the same or different. In preparing compounds wherein $R_a$ is other than hydrogen and $R_b$ is hydrogen the amino group to which $R_b$ is attached is protected with, for example, a benzyloxycarbonyl group by treatment of the corresponding derivative wherein $R_b$ is hydrogen with a benzyl haloformate, such as, benzyl chloroformate prior to treatment with the appropriate reactant described below to give compounds wherein $R_a$ is other than hydrogen. The benzyloxy group is subsequently removed by acid hydrolysis, for example, by treatment with HBr in dioxane. Of course, compounds of Formula I where $R_a$ and $R_b$ are the same may be obtained by treating the corresponding derivative wherein each of $R_a$ and $R_b$ is hydrogen with the appropriate acid halide or anhydride, alkyl haloformate or acid of the formula

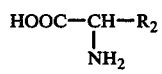
HOOC—CH—R$_2$
          |
          NH$_2$ or anhydride thereof as described below.

The compounds of general Formula I wherein $R_a$ and $R_b$ is alkylcarbonyl wherein the alkyl moiety is straight or branched and has from 1 to 4 carbon atoms are prepared by treating the corresponding derivatives wherein $R_a$ or $R_b$ is hydrogen or is suitably protected or $R_b$ is other than hydrogen as described hereinabove with an acid halide of the formula

      O
      ‖
R$_4$C—halo wherein halo is a halogen atom, for example, chlorine or bromine and R$_4$ is a straight or branched alkyl group having from 1 to 4 carbon atoms or an appropriate acid anhydride, in water in the presence of a base such as sodium hydroxide or sodium borate at a temperature of about 0° to 25° C for about ½ hour to 6 hours. When appropriate, protecting groups are removed as described hereinabove by treatment with hydrazine or acid.

The compounds of general Formula I wherein $R_a$ or $R_b$ is alkoxycarbonyl wherein the alkoxy moiety is straight or branched and has from 1 to 4 carbon atoms are prepared by treating the corresponding derivative wherein $R_a$ or $R_b$ is hydrogen or is suitably protected or $R_b$ is other than hydrogen as described hereinaboved with an alkyl haloformate of the formula

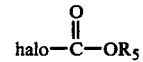
        O
        ‖
halo—C—OR$_5$ wherein halo is a halogen atom such as chlorine or bromine and R$_5$ is a straight or branched alkyl group having from 1 to 4 carbon atoms in water in the presence of a base such as sodium hydroxide or sodium borate at a temperature of about 0° to 25° C for about ½ hour to 6 hours when appropriate protecting groups are removed as described hereinabove by treatment with hydrazine or acid.

The compounds of general Formula I wherein $R_a$ or $R_b$ is

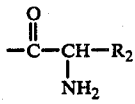

wherein $R_2$ is hydrogen, a straight or branched lower alkyl group of from 1 to 4 carbon atoms, benzyl or p-hyroxybenzyl are prepared by treating the corresponding derivative wherein $R_a$ or $R_b$ is hydrogen or is suitably protected or $R_b$ is other than hydrogen as described hereinabove with an acid of the formula

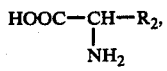

or an anhydride thereof, wherein the amino group is protected with a suitable blocking group such as benzyloxycarbonyl or tert-butoxycarbonyl and $R_2$ has the meaning defined hereinabove in an ether, such as, tetrahydrofuran or dioxane, methylene chloride or chloroform and in the presence of a dehydrating agent, such as, dicyclohexylcarbodiimide when the free acid is employed, at a temperature of about 0° to 35° C for about 1 to 12 hours followed by acid and base hydrolysis and when appropriate treatment with hydrazine to remove the protecting groups.

The individual optical isomers of compounds of Formula I wherein each of $R_a$ and $R_b$ is hydrogen may be resolved by protecting the amine distal to the halomethyl group as a phthalimido derivative using carbalkoxyphthalimidate, wherein the alkoxy moiety is, for example, a straight or branched lower alkoxy group having from 1 to 4 carbon atoms, in an ether or lower alcohol and using a (+) or (−) binaphthylphosphoric acid salt by the method of R. Viterbo et al., Tetrahedron Letters 48, 4617 (1971) or using (+) campor-10-sulfonic acid followed by treatment with hydrazine. Individual optical isomers of compounds wherein each of $R_a$ and $R_b$ is other than H may be obtained as described herein for the racemate only starting with the resolved amine or the resolved phthalimido derivative.

The compounds of general Formula IV wherein Y is $FCH_2—$ are prepared by treating a compound of the formula

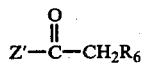 Formula VIII wherein Z' has the meaning defined in Formula IV and $R_6$ is a suitable leaving group, such as, halogen, for example, chlorine, bromine or iodine, mesylate, tosylate, triflate or trifluoroacetate with an appropriate fluorinating reagent, such as, potassium fluoride, silver fluoride, cesium fluoride, thallium fluoride, tetrabutylammonium fluoride in a suitable solvent, such as dimethoxyethane, dimethylsulfoxide, dimethylformamide, ethylene glycol, acetonitrile, acetone, benzene or hydrogen fluoride at a temperature of from about 0° to 200° C for about 2 to 48 hours. The leaving group $R_6$ may also be a diazo group in which case the fluorinating reagent employed is hydrogen fluoride/pyridine. Suitable solvent for the reaction wherein $R_6$ is a diazo group are aprotic solvents, such as, diethyl ether, tetrahydrofuran and pentane, and the reaction time varies from about 30 minutes to 24 hours at a temperature of about −20° to 65° C. illustratively, a compound of the formula

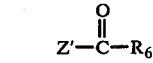

as defined above wherein $R_6$ is a diazo group in a suitable aprotic solvnt is added to a solution of hydrogen fluoride/pyridine cooled to −10° C. The reaction mixture is stirred vigorously at −10° C for 1 hour then at about 25° C for 2 hours then poured on ice. The organic phase is separated, washed with base, for example, sodium bicarbonate, dried over magnesium sulfate and concentrated under vacuum to afford an appropriate fluoromethyl ketone derivative of Formula IV.

The diazo keton derivatives, that is, the compounds of Formula VIII wherein $R_6$ is a diazo group, may be obtained from the corresponding acid halide, that is, a compound of the formula

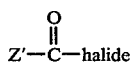

wherein halide may be, for example, chloride and Z' has the meaning defined in Formula IV by slowly adding said acid halide in an aprotic solvent, such as, diethyl ether, tetrahydrofuran pentance, hexance, benzene, dimethoxyethane or dioxane to a solution of diazomethane cooled to about −40° to 20° C in ether followed by vigorous stirring at about 25° C for about 1 to 24 hours. The thus obtained diazo ketone derivative can be isolated by standard procedures, for example, evaporation of the solvent with purification by recrystallization or chromatography or can be treated without isolation with an appropriate fluorinating reagent as described above.

The appropriately substituted diazo ketone derivative described above can also be used to prepare compounds of Formula VIII wherein $R_6$ is, for example, halogen, mesylate, tosylate, triflate, or trifluoroacetate by procedures generally known in the art. To obtain compounds of general Formula VIII wherein $R_6$ is halogen, such as, chlorine, bromine, or iodine the corresponding compound of Formula VIII wherein $R_6$ is a diazo group in a suitable aprotic solvent is treated respectively with aqueous hydrogen chloride, hydrogen bromide or hydrogen iodide. To obtain compounds of Formula VIII wherein $R_6$ is mesylate, tosylate, triflate or trifluoroacetate the corresponding diazo ketone derivative, that is, an appropriate compound of Formula VIII wherein $R_6$ is a diazo group in a suitable aprotic solvent is treated with dilute sulfuric acid to give the corresponding benzyl methanol ketone derivative which is esterified with an appropriate acid chloride or acid anhydride of methane sulfonic acid, p-toluene sulfonic acid, trifluoromethyl sulfonic acid or trifluoroacetic acid.

The acid halides, that is, compounds of the formula

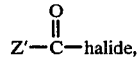

as described above, are known in the art or obtained from the corresponding acids which are known in the art or can be obtained by procedures known in the art by well known procedures, for example, by treatment of the appropriate acid with thionyl chloride in an aprotic solvent, such as, diethyl ether, tetrahydrofuran, benzene or dichloromethane at a temperature ranging from about 0° C to the reflux temperature of the solvent for about 1 to 24 hours, or treatment of the appropriate acid with oxalyl chloride in an aprotic solvent as illustrated above at a temperature of about 0° to 40° C for about 1 to 24 hours.

The compounds of general Formula IV wherein Y is FCH$_2$— and Z' is other than

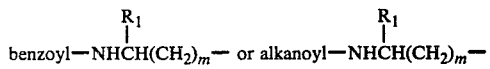
benzoyl—NHCH(CH$_2$)$_m$— or alkanoyl—NHCH(CH$_2$)$_m$— may also be obtained by treating a compound of the Formula

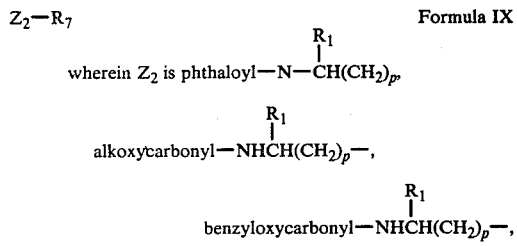

Z$_2$—R$_7$     Formula IX wherein Z$_2$ is phthaloyl—N—CH(CH$_2$)$_p$, alkoxycarbonyl—NHCH(CH$_2$)$_p$—, benzyloxycarbonyl—NHCH(CH$_2$)$_p$—, wherein p is the integer 2 or 3 and R$_1$ is hydrogen or lower alkyl of from 1 to 4 carbon atoms with the proviso that when R$_1$ is other than hydrogen p is 2, β-methylthioethyl or β-benzylthioethyl and R$_7$ is halogen, such as, chlorine, bromine or iodine, mesylate or tosylate with triphenylphosphine or tri-(lower)-alkylphosphine, for example, tri-n-butylphosphine, in a solvent such as hydrocarbons, for example, benzene or toluene or lower alcohols, such as, methanol or ethanol or acetonitrile, tetrahydrofuran, diethyl ether or dimethoxyethane at about 25° C to the reflux temperature of the solvent for about 10 minutes to 48 hours. On cooling a precipitate forms which is washed with solvent and recrystallized using, for example, ethyl acetate, acetonitrile, or a lower alcohol, for example, methanol or ethanol to give the appropriate phosphonium salt. The triphenylphosphonium or trialkylphosphonium salt is added to excess (up to 25%) sodium or lithium metal dissolved in liquid ammonia to which is added a catalytic amount of ferric nitrate with stirring for about 10 minutes to 3 hours after which the ammonia is evaporated under an inert atmosphere, such as, nitrogen or argon. An appropriate solvent, such as, benzene, toluene, diethyl ether, tetrahydrofuran or dimethoxyethane is added and the resulting substituted methylidenephosphorane is collected. The methylidenephosphorane is treated with an ester, such as, a lower alkyl, for example, methyl, ethyl, n-propyl, isopropyl or n-butyl ester of monofluoroacetic acid in a solvent such as benzene, toluene, diethyl ether, tetrahydrofuran or dimethyoxyethane under an inert atmosphere such as nitrogen or argon at a temperature of about 0° C to the reflux temperature of the solvent for about 30 minutes to 24 hours after which the reaction mixture is concentrated and distilled to give the olefin which is treated with aqueous mineral acid, such as hydrochloric or hydrobromic acid or an organic acid such as trifluoroacetic acid or p-toluene sulfonic acid using a cosolvent such as tetrahydrofuran, diethyl ether, or benzene for about 30 minutes to 24 hours at a temperature of from about 0° C to the reflux temperature of the solvent. The amount of acid employed may vary from a catalytic amount to concentrated acid.

As used in general Formula IX the term

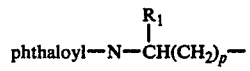
phthaloyl—N—CH(CH$_2$)$_p$— is taken to mean the group

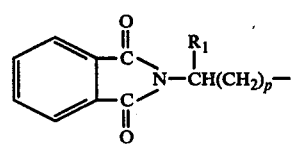

the term alkoxycarbonyl—NHCH(CH$_2$)$_p$— is taken to mean the group

alkyl—O—C—NHCH(CH$_2$)—, the term benzyloxycarbonyl—NHCH(CH$_2$)$_p$— is taken to mean the group

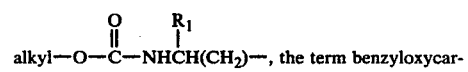

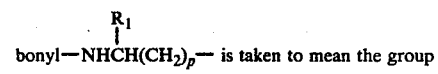

—CH$_2$OCNHCH(CH$_2$)$_p$— wherein R$_1$ and p have the meanings defined in Formula IX and alkyl is a straight or branched group of from 1 to 4 carbon atoms.

Compounds of general Formula IV wherein Y is F$_2$CH- are obtained by treating [[(methylsulfinyl)methyl]thio]methane or [[(ethylsulfinyl)methyl]thio]ethane with a suitable strong base followed by alkylation with an appropriate derivative of the formula Z'—R$_8$   Formula X wherein Z' has the meaning defined in Formula IV and R$_8$ is halogen, such as, chlorine, bromine or iodine, mesylate or tosylate, treating the thus formed Z' substituted sulfinyl derivative with a suitable strong base followed by alkylation with a suitable halomethylhalo alkylating reagent selected from chlorodifluoromethane, bromidifluoromethane, and difluoriodomethane followed by hydrolysis with aqueous acid.

Suitable strong bases which may be employed in preparing the difluoromethyl substituted ketone derivatives as described above are illustratively, sodium hydride, dilithium acetylide, lithium diisopropylamide, butyllithium, potassium tert-butoxide, sodium tert-butoxide, lithium tert-butoxide, phenyllithium, methyllithium, sodium amide, lithium amide or potassium hydride.

The alkylation reactions described in preparing the difluoromethyl ketone derivatives are carried out in a suitable solvent, such as, tetrahydrofuran, diethyl ether, hexamethylphosphortriamide, dimethylsulfoxide, or benzene at a temperature ranging from about −78° to 65° C for about 30 minutes to 24 hours. A preferred temperature for the difluoromethyl alkylation step is about 40° C. The alklyated sulfinyl intermediates are isolated by quenching with brine followed by extraction with, for example, diethyl ether, dichloromethane, or benzene.

Hydrolysis of the alkylated sulfinyl derivatives to the ketone is achieved using aqueous mineral acid, such as, hydrochloric, hydrobromic, perchloric or sulfuric in a solvent such as tetrahydrofuran, acetonitrile, diethyl ether or benzene at about −20° to 105° C, preferably about 25° C for about 30 minutes to 24 hours and preferably about 2 hours. Generally, 0.3 equivalents of mineral acid in 1.5% water is employed. The specific examples contained herein further illustrate the preparation of the difluoromethyl ketone derivatives of Formula IV.

The compounds of Formulas IX and X wherein R$_7$ and R$_8$ are halogen are known in the art or may be prepared from the appropriate carboxylic acid derivative of the formula Z$_4$—COOH   Formula XI wherein Z$_4$ is

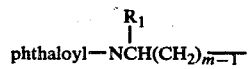

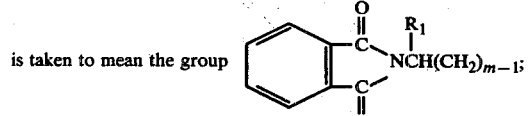

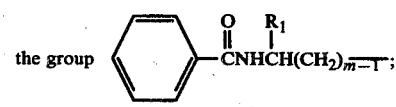

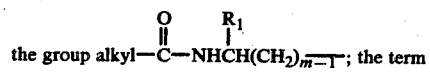

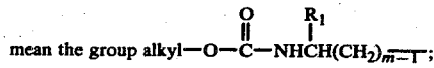

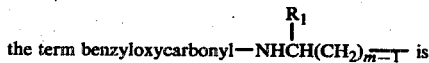

methylthiomethyl or benzylthiomethyl which acids are known in the art or may be obtained by known procedures from the corresponding unprotected amino acids which are known in the art or readily obtained by procedures known in the art. The compounds of Formulas IX and X wherein R$_7$ and R$_8$ are mesylate or tosylate may be prepared by treating the corresponding derivatives wherein R$_7$ or R$_8$ are halogen with a metal salt for example, the sodium salt of methane sulfonic acid or p-toluene sulfonic acid.

As used in Formula XI the term phthaloyl—NCH(CH$_2$)$_{\overline{m-1}}$—
         |
         R$_1$ is taken to mean the group

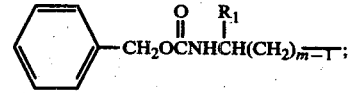

the term benzoyl—NHCH(CH$_2$)$_{\overline{m-1}}$— is taken to mean the group

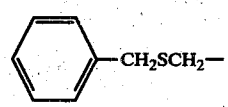—CNHCH(CH$_2$)$_{\overline{m-1}}$—;

the term alkanoyl—NHCH(CH$_2$)$_{m-1}$— is taken to mean the group alkyl—C—NHCH(CH$_2$)$_{\overline{m-1}}$—; the term alkoxycarbonyl—NHCH(CH$_2$)$_{\overline{m-1}}$— is taken to mean the group alkyl—O—C—NHCH(CH$_2$)$_{\overline{m-1}}$—;

the term benzyloxycarbonyl—NHCH(CH$_2$)$_{\overline{m-1}}$— is taken to mean the group

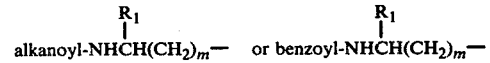

the term methylthiomethyl is taken to mean the group CH$_3$SCH$_2$—; and the term benzylthiomethyl is taken to mean the group

[benzene ring]—CH$_2$SCH$_2$— wherein alkyl is a straight or branched group having from 1 to 4 carbon atoms, m is the integer 2 or 3, and R$_1$ is hydrogen or a lower alkyl group having from 1 to 4 carbon atoms with the proviso that when R$_1$ is other than hydrogen, m is the integer 2.

The compounds of general Formula IV wherein Y is F$_3$C— are prepared by treating a compound of Formula X wherein R$_8$ is halogen and Z' is other than β-methylthioethyl, alkanoyl-NHCH(CH$_2$)$_m$—   or   benzoyl-NHCH(CH$_2$)$_m$—
         |                                      |
         R$_1$                                   R$_1$ with triphenylphosphine or a tri-(lower)alkylphosphine, such as, tri-n-butylphosphine in a solvent, such as, hydrocarbons, for example, benzene or toluene or lower alcohols, such as, methanol or ethanol, or acetonitrile, tetrahydrofuran, diethyl ether, or dimethoxyethane at about 25° C to the reflux temperature of the solvent for about 10 minutes to 48 hours. On cooling a precipitate forms which is washed with solvent and recrystallized using, for example, ethylacetate, acetonitrile or a lower alcohol to give the appropriate Z' substituted phosphonium salt. The appropriate Z' substituted triphenylphosphonium salt or tri-(lower)alkylphosphonium salt is added to excess (up to 25%) sodium or lithium metal dissolved in liquid ammonia to which is added a catalytic amount of ferric nitrate with stirring for about 10 minutes to 3 hours after which the ammonia is evaporated under an inert atmosphere, such as, nitrogen or argon. An appropriate solvent, such as, benzene, toluene, diethyl ether, tetrahydrofuran or dimethoxyethane is added and the resulting substituted methylidenephosphorane is collected. The methylidenephosphorane phosphorane is treated with an ester, such as, a lower alkyl, for example, methyl, ethyl, n-propyl, isopropyl or n-butyl ester of trifluoroacetic acid in a solvent such as benzene, toluene, diethyl ether, tetrahydrofuran or dimethoxyethane under an inert atmosphere such as nitrogen or argon at a temperature of about 0° C to the reflux temperature of the solvent for about 30 minutes to 24 hours after which the reaction mixture is concentrated and distilled to give the olefin which is treated with aqueous mineral acid, such as hydrochloric or hydrobromic acid or an organic acid such as trifluoroacetic acid or p-toluene sulfonic acid using a cosolvent such as tetrahydrofuran, diethyl ether, or benzene for about 30 minutes to 24 hours at a temperature of from about 0° C to the reflux temperature of the solvent. The amount of acid employed may vary from a catalytic amount to concentrated acid.

The compounds of general Formula III are prepared by reacting a compound of the formula

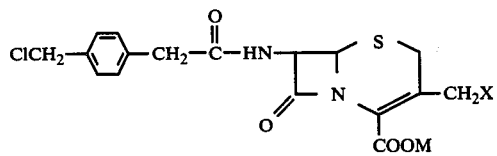

Formula XII wherein X and M have the meanings defined in general Formula III, which compounds are prepared as described in U.S. Pat. No. 3,919,206 which patent is incorporated herein by reference thereto, with a compound of general Formula I wherein each of $R_a$ and $R_b$ is hydrogen and the amino group distal to the Y substituent is protected with a suitable blocking group such as tert-butoxycarbonyl. The reaction is generally carried out in a solvent, such as, a lower alcohol, for example, methanol, ethanol or isopropyl alcohol, or dimethylsulfoxide, dimethylformamide or aqueous mixtures of these solvents. The temperature of the reaction may vary from about 0° to 125° C and the reaction time may vary from about one-half hour to 24 hours. Following the solvolysis reaction the amino protecting group is removed by acid hydrolysis, and the cephalosporin products are isolated by conventional procedures.

The following Example 1 illustrates the use of a compound of general Formula I wherein $R_a$ and $R_b$ are hydrogen as a chemical intermediate in the preparation of a cephalosporin of Formula III.

EXAMPLE 1

7-[[2-[4-(1-difluoromethyl-4-aminobutylaminomethyl)-phenyl]-acetyl]amino]-3-acetyloxymethyl-8-oxo-5-thia-1-azabicyclo-[4.2.0]oct-2-ene-2-carboxylic acid A mixture of 1 g of 3-acetyloxymethyl-7-[[2-[4-(chloromethyl)phenyl]acetyl]amino]-8-oxo-5-thia-1-azabicyclo[4.2.0]oct-2-ene-2-carboxylic acid and 1 g of 1-difluoromethyl-1,4-butanediamine wherein the amino group distal to the Y substituent is protected with tert-butoxycarbonyl in 50 ml of ethanol was stirred at 25° C for 24 hours after which the solvent is removed leaving a residue which is treated with mild acid and chromatographed on silica gel using benzene-acetone as the eluant to give 7-[[2-[4-(1-difluoromethyl-4-aminobutylaminomethyl)phenyl]-acetyl]amino]-3-acetyloxymethyl-8-oxo-5-thia-1-azabicyclo-[4.2.0]oct-2-ene-2-carboxylic acid.

EXAMPLE 2

An illustrative composition for hard gelatin capsules is as follows:

| (a) 1-difluoromethyl-1,4-butanediamine | 20 mg |
|---|---|
| (b) talc | 5 mg |
| (c) lactose | 90 mg |

The formulation is prepared by passing the dry powders of (a) and (b) through a fine mesh screen and mixing them well. The powder is then filled into hard gelatin capsules at a net fill of 115 mg per capsule.

EXAMPLE 3

An illustrative composition for tablets is as follows:

| (a) 1-fluoromethyl-1,5-pentanediamine | 20 mg |
|---|---|
| (b) starch | 43 mg |
| (c) lactose | 45 mg |
| (d) magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 110 mg each.

EXAMPLE 4

An illustrative composition for an injectable suspension is the following 1 ml ampul for an intramuscular injection.

| | | Weight per cent |
|---|---|---|
| (a) | 1-difluoromethyl-3-methylthiopropylamine | 1.0 |
| (b) | polyvinylpyrrolidone | 0.5 |
| (c) | lecithin | 0.25 |
| (d) | water for injection to make | 100.0 |

The materials (a)-(d) are mixed, homogenized and filled into 1 ml ampuls which are sealed and autoclaved 20 minutes at 121° C. Each ampul contains 10 mg per ml of novel compound (a).

The following examples further illustrate the compounds of the invention.

EXAMPLE 5

1-Fluoromethyl-1,4-butanediamine dihydrochloride (A) To a solution of 40 mmole of diazomethane in 110 ml of ether cooled to 0° C and magnetically stirred is added under nitrogen dropwise over a period of 1 hour a solution of 20 ml of 4-phthalimidobutyryl chloride in 75 ml of ether. Stirring is continued for 1 hour at 25° C after which the reaction mixture is added to a solution of 40 ml of HF/pyridine precooled to 0° C. The resulting heterogeneous mixture is stirred at 25° C for 1-½ hours and then poured on ice water. The ether phase is separated, washed with a solution of bicarbonate, then with brine and dried over magnesium sulfate. Concentration of the solvent under reduced pressure affords a solid which is recrystallized from diethylether/pentane to give fluoromethyl 3-phthalimidopropyl ketone, m.p. 92° C.

(B) To a solution of 550 mg (2.2 mmole) of fluoromethyl 3-phthalimidopropyl ketone in a mixture of 5 ml of tetrahydrofuran and 5 ml of methanol cooled to −20° C is added a solution of 0.8 mmole of sodium borohydride in a mixture of 5 ml of tetrahydrofuran and 5 ml of methanol precooled to −20° C. The reaction mixture is stirred for 15 minutes at −20° C and then neutralized with 2 M HCl to a pH of 1. The solvents are evaporated under reduced pressure and the residue is partitioned between water and chloroform. The organic phase is washed with brine, dried over magnesium sulfate and concentrated to give a residue which is recrystallized from tetrahydrofuran-diethylether to afford 1-fluoro-5-phthalimido-2-pentanol, m.p. 85° C. A mixture of 264 mg (1.05 mmole) of 1-fluoro-5-phthalimido-2-pentanol, 170 mg (1.05 mmole) of the phthalimide, 302 mg (1.05 mmole) of triphenylphosphine and 201 mg (1.15 mmole) of diethylazodicarboxylate in 8 ml of tetrahydrofuran is stirred under nitrogen for 2 hours at 25° C. The solvent is evaporated under reduced pressure and the residue taken up in benzene. The insoluble material is discarded and the residue obtained after concentration of the filtrate is recrystallized from tetrahydrofuran-diethylether to give 1-fluoromethyl-1,4-butanediyl-bis-phthalimide, m.p. 112° C. A suspension of 3.1 g of 1-fluoromethyl-1,4-butanediyl-bis-phthalimide in 140 ml of concentrated HCl is heated at reflux temperature for 3 days. The phthalic acid which precipitates on cooling to 4° C is filtered off. The filtrate is concentrated to about 20 ml and cooled to 4° C. The remaining phthalic acid which separates is filtered off and the filtrate is concentrated under reduced pressure. The residue is treated with 40 ml of boiling isopropyl alcohol 3 times and then recrystallized from absolute ethanol to give 1-fluoromethyl-1,4-butanediamine dihydrochloride, m.p. 154° C.

When in the procedure of Example 5 (A) an appropriate amount of 5-phthalimidovaleryl chloride, 4-phthalimidovaleryl chloride, 6-n-butoxycarbonylaminocapryl chloride, 3-methylthiopropionyl chloride or 3-benzylthiopropionyl chloride is substituted for 4-phthalimidobutyryl chloride the following ketone compounds are obtained:
fluoromethyl 4-phthalimidobutyl ketone,
fluoromethyl 3-phthalimidobutyl ketone,
fluoromethyl 3-n-butoxycarbonylaminobutyl ketone,
fluoromethyl 2-methylthioethyl ketone, and
fluoromethyl 2-benzylthioethyl ketone.

EXAMPLE 6

Difluoromethyl 3-phthalimidopropyl ketone

A solution of 10 mmole of [((ethylsulfinyl)methyl)-thio]ethane in 20 ml of tetrahydrofuran is treated with 10 mmole of sodium hydride at 25° C for 2 hours after which 10 mmole of N-(3-bromopropyl)phthalimide in 5 ml of tetrahydrofuran is added. The reaction mixture is stirred overnight at 25° C then quenched with brine and extracted with chloroform. The organic phase is washed with brine, dried over magnesium sulfate and concentrated under reduced pressure. The residue is purified by chromotography on silica gel to give N-(4-ethylthio-4-ethylsulfinylbutyl)phthalimide. To a solution of 22 mmole of N-(4-ethylthio-4-ethylsulfinyl-butyl)phthalimide in 20 ml of tetrahydrofuran is added under nitrogen at 0° C a solution of lithium diisopropylamide in 23 mmole of tetrahydrofuran. The reaction mixture is stirred for 30 minutes at 25° C then is saturated with difluorochloromethane. Stirring is continued for 2 hours at 40° C. After quenching with brine, the reaction mixture is extracted with ether. The organic phase is decanted, washed with brine, dried over magnesium sulfate and concentrated under reduced pressure to give N-(4-ethylthio-4-ethylsulfinyl-4-difluoro-methylbutyl)phthalimide. To a solution of 30 mole of N-(4-ethylthio-4-ethylsulfinyl-4-difluoromethylbutyl)-phthalimide in 33 ml of acetonitrile is added at 0° C 1.1 ml of a 70% aqueous solution of perchloric acid. After stirring for 2 hours at 0° C the reaction mixture is poured into 60 ml of water then extracted with chloromethane. The organic phase is washed with brine, dried, filtered and the filtrate concentrated under reduced pressure to afford difluoromethyl 3-phthalimidopropyl ketone.

When in the procedure of Example 6 an appropriate amount of N-(4-bromobutyl)phthalimide, N-(1-methyl-3-bromopropyl)butyramide, 2-methylthioethylbromide or 2-benzylthioethylbromide is substituted for N-(3-bromopropyl)-phthalimide the following respective ketone compounds are obtained:
difluoromethyl 4-phthalimidobutyl ketone,
difluoromethyl 3-n-propylcarbonylaminobutyl ketone,
difluoromethyl 2-methylthioethyl ketone, and difluoromethyl 2-benzylthioethyl ketone.

EXAMPLE 7

Trifluoromethyl 3-phthalimidopropyl ketone

A mixture of 20 mmole of N-(3-bromopropyl)phthalimide and 22 mmole of triphenylphosphine in 50 ml of benzene is heated at reflux temperature for 2 days. The solid which separates on cooling is filtered, washed with benzene and dried under reduced pressure to give 3-phthalimidopropyl triphenylphosphonium bromide. To a solution of 100 ml of dry liquid ammonia is added finely divided sodium (0.46 g or $2 \times 10^{-2}$ M) and a catalytic amount of ferric nitrate. When the blue sodium solution turns gray 10 g or $2 \times 10^{-2}$ M of finely powdered 3-phthalimidopropyltriphenylphosphonium bromide is added. After stirring for 15 minutes the ammonia is evaporated under a stream of nitrogen. To the residue is added 100 ml of anhydrous benzene and the solution is boiled for about 10 minutes under nitrogen. The solid residue is filtered pff and to the filtrate, containing salt free 3-phthalimidopropylidene triphenylphosphorane is added 6.6 g of $5 \times 10^{-2}$ M of ethyl trifluoroacetate. The reaction mixture is heated at reflux temperature under nitrogen for 12 hours. Concentration of the solvent leaves a residue which is distilled under high vacuum to afford 2-ethoxy-1,1,1-trifluoro-5-phthalimidopent-2ene. A solution of 3 g of 2-ethoxy-1,1,1-trifluoro-5-phthalimidopent-2-ene in 50 ml of ether is treated with a solution of 1 M of sulfuric acid in 50 ml of water. The reaction mixture is stirred for one half hour at 25° C. The ether phase is separated, washed with brine, and dried over magnesium sulfate and concenrated to give trifluoromethyl 3-phthalimidopropyl ketone.

When in the procedure of Example 7 an appropriate amount of N-(4bromobutyl)phthalimide, N-(1-methyl-3-bromopropyl)butyramide, or 2-benzylthioethyl bromide is substituted for N-(3-bromopropyl)phthalimide the following respective ketone compounds are obtained:
trifluoromethyl 4-phthalimidobutyl ketone,
trifluoromethyl 3-benzyloxycarbonylaminobutyl ketone,
trifluoromethyl 2-benzylthioethyl ketone.
When in the procedure of Example 5 (B) an appropriate amount of
difluoromethyl 3-phthalimidoproyl ketone,
difluoromethyl 4-phthalimidobutyl ketone,
difluoromethyl 3-n-propylcarbonylaminobutyl ketone,
difluoromethyl 2-methylthioethyl ketone,
difluoromethyl 2-benzylthioethyl ketone,
fluoromethyl 4-phthalimidobutyl ketone,
fluoromethyl 3-phthalimidobutyl ketone,
fluoromethyl 3-n-butoxycarbonylaminophentyl ketone,
fluoromethyl 2-methylthioethyl ketone,
fluoromethyl 2-benzylthioethyl ketone,
trifluoromethyl 3-phthalimidopropyl ketone,
trifluoromethyl 4-phthalimidobutyl ketone,
trifluoromethyl 3-benzyloxycarbonylaminobutyl ketone, or
trifluoromethyl 2-benzylthioethyl ketone
is substituted for fluoromethyl 3-phthalimidopropyl ketone the following respective rproducts are obtained:
1-difluoromethyl-1,4-butanediamine hydrochloride,
1-difluoromethyl-1,5-pentanediamine hydrochloride,
1-difluoromethyl-1,4-pentanediamine hydrochloride,
1-difluoromethyl-3-methylthiopropanemine hydrochloride,
1-difluoromethyl-3-benzylthiopropaneamine hydrochloride,
1-fluoromethyl-1,5-pentanediamine hydrochloride,
1-fluoromethyl-1,4-pentanediamine hydrochloride,
1-fluoromethyl-1,4-hexanediamine hydrochloride,
1-fluoromethyl-3-ethylthiopropaneamine hydrochloride,
1-fluoromethyl-3-benzylthiopropaneamine hydrochloride,
1-trifluoromethyl-1,4-butanediamine hydrochloride,
1-trifluoromethyl-1,5-pentanediamine hydrochloride,
1-trifluoromethyl-1,4-pentanediamine hydrochloride, and
1-trifluoromethyl-3-benzylthiopropane amine hydrochloride.

EXAMPLE 8

5'-Desoxy-5'-[S-(3-difluoromethyl-3-aminopropyl)-S-methyl)thio]adenosine

To 10 mmole of sodium amide in 200 ml of ammonia is added 10 mmole of 1-difluoromethyl-3-benzylthiopropane-amine. After 1 hour sodium metal in small pieces is added until the blue color persists for 5 minutes then 10 mmole of 2',3'-isopropylidene-5'-$p$-toluenesulfonyl-adenosine is added. After 2 hours the ammonia is allowed to evaporate, and the remaining residue is treated with 1 M sulfuric acid for 48 hours at 25° C after which the pH is adjusted to 6 and the solution is applied to an ion exchange resin, KV-2NH$_4$+ and then a DEAE cellulose (OH$^-$) column. The aqueous eluant is evaporated and the residue recrystallized from water/ethanol to give the 5'-desoxy-5' compound. The adenosine derivative is dissolved in a mixture of 4 ml of acetic acid and 4 ml of formic acid after which 1 ml of methyl iodide is added. The mixture is maintained under a nitrogen atmosphere for 6 days at 25° C then the solvents are removed under reduced pressure at 25° C. The resulting residue is dissolved in 8 ml of 0.1 M HCl, and a saturated solution if Reinecke salt is added. The resulting precipitate is collected and treated with 1.5 g of silver sulfate in acetone at 25° C for 36 hours. The insoluble residue is filtered off and washed with methanol. The combined filtrates are concentrated under reduced pressure to yield 5'-desoxy-5'-[S-(3-difluoromethyl-3-aminopropyl)-S-(methyl)thio]adenosine.

EXAMPLE 9

N-(1Difluoromethyl-4-guanidinobutyl)acetamide

To a solution of 10 mmole of N-(1-difluoromethyl-4-aminobutyl)acetamide in 10 ml of methanol and 10 ml of water is added 20 mmole of ethyl isothiouronium hydrobromide. The pH of the solution is maintained at 10 by the addition of 2 M sodium hydroxide solution during 48 hours at 25° C after which the methanol is evaporated and the aqueous solution extracted well with dichloromethane. The organic phase is dried and evaporated to afford N-(1-difluoromethyl-4-guanidino-butyl)acetamide.

When in the above procedure an appropriate amount of benzyl N-(1-difluoromethyl-4-aminobutyl)carbamate is substituted for N-(1-difluoromethyl-4-aminobutyl)acetamide, benzyl N-(1-difluoromethyl-4-guanidinobutyl)carbamate is obtained which upon treatment with HBr in dioxane (20 ml of a 40% (w/w) solution) for 30 minutes at 28° C and followed by the addition of ether affords 1-difluoromethyl-4-guanidinobutylamine.

EXAMPLE 10

N-(4-Fluoromethyl-4-aminobutyl)-2-aminopropionamide di-hydrobromide

A solution of 2 mmole of N-(1-fluoromethyl-4-aminobutyl)benzyl carbamate in 4 ml of dichloromethane is treated with 2 mmole of N-carbobenzoxyalanine and 2 mmole of N,N'-dicyclohexylcarbodiimide for about 15 hours at 25° C after which the solution is cooled to 0° C and the precipitated dicyclohexylurea filtered off. The filtrate is diluted with 20 ml of dichloromethane and washed with 1 N hydrochloric acid, water and aqueous sodium bicarbonate, then dried and concentrated. The resulting residue is treated with 6 ml of a 40% (w/w) solution of hydrogen bromide in dioxane at 25° C for 30 minutes then diluted with ether and the precipitated N-(4-fluoromethyl-4-aminobutyl)-2-amino-propionamide dihydrobromide collected.

EXAMPLE 11

N-(4Fluoromethyl-4-aminobutyl)acetamide hydrobromide

A solution of 2 mmole of N-(1-fluoromethyl-4-aminobutyl)benzyl carbamate in 10 ml of chloroform is treated with 2 mmole of triethylamine followed by 160 mg (2.1 mM) of acetyl chloride. After 1 hour at 25° C the solution is washed with water, dilute hydrochloric acid, and aqueous sodium carbonate, then dried and concentrated. The resulting residue is treated with 6 ml of a 40% (w/w) solution of hydrogen bromide in dioxane for 30 minutes at 25° C, then ether is added and the precipitated N-(4-fluoromethyl-4-aminobutyl)acetamide hydrobromide is collected.

When in the above procedure an appropriate amount of ethyl chloroformate is substituted for acetyl chloride, N-(4-fluoromethyl-4-aminobutyl)ethyl carbamate is obtained.

EXAMPLE 12

N-)1-Fluoromethyl-4-aminobutyl)acetamide

A solution of 1 mmole of N-(4-fluoromethyl-4-aminobutyl)phthalimide in 10 ml of chloroform is treated with 1 ml of triethylamine followed by 78 mg (1 mM) of acetyl chloride in 5 ml of chloroform. After 1 hour at 25° C the solution is washed with water, dried and concentrated. The resulting residue is dissolved in 10 ml of ethanol and treated with 60 mg (1.1 mM) of hydrazine hydrate at reflux for 2 hours after which the solvent is evaporated. The residue is treated with 1 N sodium hydroxide solution until the solid dissolves then is extracted with dichloromethane. The organic phase is dried and concentrated to give N-(1-fluoromethyl-4-aminobutyl)-acetamide.

N-(4-Fluoromethyl-4-aminobutyl)phthalimide used in the above procedure is prepared as follows. A solution of 13.5 g (61.6 mM) of carbethoxyphthalimide in 70 ml of tetrahydrofuran is added dropwise to a solution of 61.6 mmole of 1-fluoromethyl-1,4-butanediamine in 30 ml of tetrahydrofuran in an ice-bath. After completion of the addition the mixture is stirred for 2 hours at 25° C then diluted with ether, and the solution is extracted with 1 N hydrochloric acid (3 × 100 ml). The aqueous phase is washed several times with ether then concentrated to dryness leaving a residue which is recrystallized from ethanol to give N-(4-fluoromethyl-4-aminobutyl)phthalimide HCl which is converted to the free base by known procedures.

When in the procedure of Example 12 an appropriate amount of ethyl chloroform is used in place of acetyl chloride, N-(1fluoromethyl-4-aminobutyl)ethyl carbamate is obtained.

When in the procedure of Example 12 an appropriate amount of benzyl chloroform is substituted for acetyl chloride, N-(1-fluoromethyl-4 -aminobutyl)benzyl carbamate is obtained.

EXAMPLE 13

N-(1-Fluoromethyl-4-aminobutyl)-2-aminopropionamide dihydrobromide

A solution of 2 mmole of N-carbobenzoxyalanine in 10 ml of dichloromethane is treated with 2 mmole of triethylamine followed by 2 mmole of ethyl chloroformate. After 1 hour at 25° C the solution is treated with 2 mmole of N-(4-fluoromethyl-4-aminobutyl)phthalimide in 10 ml of chloroform and maintained at 25° C for one hour after which the solution is washed with 1 N hydrochloric acid, water and aqueous sodium carbonate then dried and concentrated. The residue is dissolved in 15 ml of ethanol and treated with 100 mg (2 mM) of hydrazine hydrate at reflux for 2 hours after which the solvent is evaporated. The residue is treated with 5% aqueous sodium hydroxide and extracted with dichloromethane. The organic phase is dried and concentrated and the resulting residue is treated with 5 ml of a 40% (w/w) solution of hydrogen bromide in dioxane. After 30 minutes at 25° C the mixture is treated with ether and the precipitated N-(1-fluoromethyl-4-aminobutyl)-2-aminopropionamide dihydrobromide collected.

EXAMPLE 14

1-Fluoromethyl-1,4-butylene-bis-2-aminopropionamide dihydrobromide

A solution of 4 mmole of N-carbobenzoxyalanine in 10 ml of dichloromethane is treated with 4 mmole of triethylamine followed by 4 mmole of ethyl chloroformate. After 1 hour at 25° C the solution is treated with 2 mmole of 1-fluoromethyl-1,4-butanediamine in 5 ml of dichloromethane. The solution is maintained at 25° C for 1 hour then is washed with water, dried and concentrated. The resulting residue is treated with 6 ml of a 40% (w/w) solution of hydrogen bromide in dioxane for 30 minutes at 25° C then diluted with ether. The precipitate is collected to afford 1-fluoromethyl-1,4-butylene-bis-2-aminopropionamide dihydrobromide.

EXAMPLE 15

1-Fluoromethyl-1,4-butylene-bis-acetamide

A solution of 4.5 mmole of 1-fluoromethyl-1,4-butanediamine in 50 ml of ether containing 0.91 g (9.0 mM) of triethylamine is treated with 0.7 g (9.0 mM) of acetyl chloride. After 1 hour the ether solution is washed with brine, dried and evaporated to afford 1-fluoromethyl-1,4-butylene-bis-acetamide.

When in the above procedure an appropriate amount of ethyl chloroformate is substituted for acetyl chloride, diethyl 1-fluoromethyl-1,4-butylene-bis-carbamate is obtained.

We claim:

1. A compound of the formula

wherein Y is $FCH_2—$, $F_2CH—$, or $F_3C—$; Z is $\beta$-methylthioethyl, $\beta$-benzylthioethyl, S-(5'-desoxyadenosin-5'-yl)-S-methylthioethyl, $\gamma$-guanidinopropyl or

wherein n is the integer 2 or 3 and $R_1$ is hydrogen or a lower alkyl group of from 1 to 4 carbon atoms with the proviso that when $R_1$ is other than hydrogen, n is 2; each of $R_a$ and $R_b$ is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched or the group

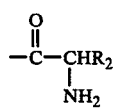

wherein $R_2$ is hydrogen, a straight or branched lower alkyl group of from 1 to 4 carbon atoms, benzyl or p-hydroxybenzyl; with the provisos that when Z is β-benzylthioethyl or S-(5'-desoxyadenosin-5'-yl)-S-methylthioethyl, $R_b$ is hydrogen, when Z is β-methylthioethyl, Y is other than $F_3C-$, and when Z is

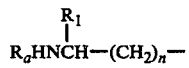

each of $R_a$ and $R_b$ can be the same or different; and pharmaceutically acceptable salts and individual optical isomers thereof.

2. A compound of claim 1 wherein Z is β-methylthioethyl, S-(5'-desoxyadenosin-5'-yl)-S-methylthioethyl, γ-guanidinopropyl or

3. A compound of claim 1 wherein each of $R_a$ and $R_b$ is hydrogen.

4. A compound of claim 1 wherein Z is

5. A compound of claim 4 wherein each of $R_a$ and $R_b$ is hydrogen.

6. A compound of claim 5 wherein $R_1$ is hydrogen or methyl.

7. A compound of claim 1 wherein Y is $FCH_2-$ or $F_2CH-$.

8. A compound of claim 5 which is 1-difluoromethyl-1,4-butanediamine.

9. A compound of claim 5 which is 1-difluoromethyl-1,4-pentanediamine.

10. A process for preparing a compound of claim 1 wherein Z is β-methylthioethyl, β-benzylthioethyl or

and each of $R_a$ and $R_b$ is hydrogen which comprises reducing a ketone of the formula

wherein Z' is phthaloyl—$\overset{R_1}{\underset{|}{N}}CH(CH_2)_m-$,

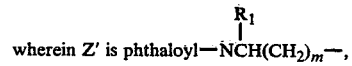

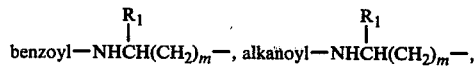

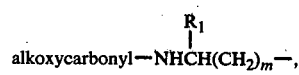

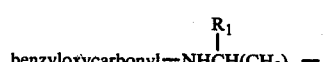

β-methylthioethyl or β-benzylthioethyl wherein m is the integer 2 or 3, the alkanoyl moiety has from 2 to 5 carbon atoms and is straight or branched, the alkoxy moiety has from 1 to 4 carbon atoms and is straight or branched and Y and $R_1$ have the meanings defined in claim 1 with the proviso that when Y is $F_3C-$, Z' is other than β-methylthioethyl

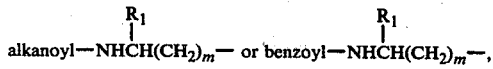

to the corresponding alcohol which is treated with one equivalent of an appropriate imide, 1.1 equivalents of an appropriate phosphine and 1.1 equivalents of diethyl azodicarboxylate in a suitable solvent at about 0° to 100° C for about 1/2 hour to 24 hours under an inert atmosphere followed by hydrolysis to the amine.

* * * * *